(12) United States Patent
Gitis et al.

(10) Patent No.: US 6,502,455 B1
(45) Date of Patent: Jan. 7, 2003

(54) MICROSCRATCH TEST INDENTER AND METHOD OF MICROSCRATCH TESTING

(75) Inventors: Norm Gitis, Cupertino, CA (US); Michael Vinogradov, Sunnyvale, CA (US)

(73) Assignee: Center for Tribology, Inc., Campbell, CA (US)

( * ) Notice: Subject to any disclaimer, the term of this patent is extended or adjusted under 35 U.S.C. 154(b) by 0 days.

(21) Appl. No.: 09/668,551

(22) Filed: Sep. 25, 2000

(51) Int. Cl.⁷ .................................................. G01N 3/24

(52) U.S. Cl. ..................................................... 73/150 A

(58) Field of Search ........................... 73/9, 78, 81, 82, 73/85, 150 R, 801, 150 A

(56) References Cited

U.S. PATENT DOCUMENTS 5,696,327 A   12/1997   Huang et al.

OTHER PUBLICATIONS

Microphotonics, Tester CSEM, Irvine, CA, USA, Aug. 2000.

*Primary Examiner*—Robert Raevis

(57) ABSTRACT

A method and an indenter for microscratch test of durability properties of the materials, including resistance of coating films to delamination. The blade-like indenter has a prism-like body defined by a front side, a rear side, a first lateral side, and a second lateral side. The first lateral side and the second lateral side converge and form at their intersection an edge that extends from the front side to the rear side. An angle between the edge and the front side is sharp, and an angle between the first lateral side and the second lateral side is rounded with a radius. During the test, the blade-like indenter is installed at selected angles of attack to the surface of the test material; a relative movement is created between the indenter and the test material with simultaneous mechanical, electrical, and acoustical measurements. Analysis of the test results has confirmed that the micro-blade of the invention with two variable attack angles is the most effective indenter for both scratch resistance and adhesion evaluations, as compared to conventional indenters, such as sharp conical tips. The test method includes monitoring various mechanical, electrical and acoustic parameters of the indenter-to-surface interactions and their mutual correlation for durability evaluation.

13 Claims, 5 Drawing Sheets

MICROSCRATCH TEST INDENTER AND METHOD OF MICROSCRATCH TESTING

FIELD OF THE INVENTION

The present invention relates to the field of microtribology, in particular to a test indenter for microtribological measurements of durability via microscratch and adhesion tests. The invention also relates to a method of microscratch testing. The invention may find its use for studying and testing durability, wear and scratch resistance, adhesion and delamination resistance of solid surfaces, coatings and films, as well as near-surface layers of various materials, including metals, composites, polymers, ceramics, etc.

BACKGROUND OF THE INVENTION

Durability of surfaces of various materials is characterized by their wear and scratch resistance. If the surfaces are formed by coatings or films, another important characteristic of their durability is an adhesive strength with which the coating film is attached to either a substrate or an underlayer, and its delamination resistance. In combination, the aforementioned characteristics constitute a unique signature of the surface or coating.

The use of coating films, both thin and thick, in various industries is increasing constantly. Thin films are used extensively in such fields as magnetic and electronic materials. For example, a hard disk used in computer disk drives comprises either an aluminum alloy or a glass substrate, coated with a multi-layered structure of various materials, including a nickel-phosphorous layer of several micron thickness, magnetic layer(s) of a fraction of micron thickness, and then a carbon overcoat less than a dozen nanometer thick. Both scratch resistance of the top carbon layer and delamination resistance, or adhesion, of each of the layers are matters of great importance for the drive durability.

Another example of thin film application is microelectronic where thin films are applied to a silicon substrate and, with photolithography and etching, are formed into well defined fine lines used as conductive interconnections between elements of semiconductor chips. In this case the durability of the microelectronic devices depends on the delamination resistance, or adhesion, of thin films to their substrates. An example of a thick coating is paint, applied to various surfaces of automotive vehicles. The paint has to be scratch resistant, at the same time having good delamination resistance, or adhesion, to its metal or non-metal substrate. When paint includes two or three layers, for example an under-layer, color layer and transparent overcoat, the delamination resistance of each of the layers is an important characteristic of the durability. Another example is a coating on optical lenses, which may include anti-reflective and wear-resistant layers; the lenses durability is defined by both scratch resistance of the surface and delamination resistance, or adhesion strength, of each of the coated layers.

Therefore, there has been continued development in the art to evaluate surface durability by measuring such surface properties as resistance to scratch, or wear resistance, and resistance of coating films to delamination, or adhesive strength.

The most typical test, which finds wide applications for measuring the above properties, is known as a microscratch test. It is an ideal method for characterizing the surface durability, including that of films and coatings. The microscratch test can be used for all kinds of industrial coatings from thin films in semiconductor and optical industries to decorative and protective coatings for consumer goods. The microscratch test consists in that a scratching indenter, typically either steel or diamond conical tip or stylus, is pressed into the tested material under a known constant or progressively increasing applied normal load, and a relative motion is caused between the indenter and the tested surface, while evaluating the aforementioned characteristics by monitoring friction and acoustic signals.

Known in the art is a microscratch tester of CSEM, sold by Micro Photonics, Irvine, Calif., USA. The technique involves generating a controlled scratch with a conical point indenter, either a Rockwell C diamond tip or a sharp steel tip, drawn across a coated surface under either a constant or a progressively increasing load. This is schematically shown in FIG. 1, which is a side view of the test indenter 10 on the coating 12 during the test. When the coating 12 starts to fail, the corresponding critical load is detected by means of an acoustical sensor attached to an indenter holder, friction force between the indenter and the surface, penetration depth, and by optical microscopy (not shown in FIG. 1). Once known, the critical load is used to quantify the scratch resistance and adhesion properties of the film-substrate combinations.

In this test, the indenter is held perpendicular to the surface of the material being tested, and during dragging the applied load is kept normal to the test surface. A disadvantage of such point tips is that the end of the indenter is very sharp, with an extremely small radius (of about 1 to 20 $\mu$m). So, when the tip is pressed into the surface of the tested coating, it develops a very high contact pressure, and even when it does not break through the coating yet, it produces significant stresses deep in the substrate. So, the test results are affected by the properties of the substrate, which makes it impossible to accurately measure the properties of thin films and coatings.

U.S. Pat. No. 5,696,327 issued in 1997 to He Huang et al. describes a microscratch test conducted with the use of a blade-type indenter, as compared with the above mentioned point microscratch test with a conical tip. In this patent, a blade-type indenter is used to facilitate calculation of the adhesion work of delamination in a two-dimensional representation, as compared to the uni-dimensional representation in the point microscratch test. The test is carried out by pressing an indenter onto a coating and moving either blade or the test sample in relation to each other, with simultaneous application of both normal load and lateral force to the indenter.

The blade-type indenter used for the above test has a symmetrical wedge-shaped cross section with front and back attack angles equal to each other. The blade is held perpendicular to the tested surface and is made from a diamond or sapphire. Accuracy of determining the adhesion work is achieved by utilizing a blade of significant width, so that the data is taken from essentially macroscopic surface areas. Such blade-type indenter is not suitable for testing small local areas or thin films or multi-layered materials. Furthermore, the method of U.S. Pat. No. 5,696,327 requires preparation of special test samples with a width narrower than the width of the blade. In addition, the test data is extremely sensitive to the blade orientation, which requires ultra-precision adjustment of the cutting edge of the blade to be parallel to the tested surface.

In the known scratch test methods, only friction and acoustic measurements were combined together, whereas another known test method with measurements of electric properties (impedance, resistance, capacitance) may be carried out separately, in combination with vertical indentation test, particularly because of non-conductivity of the diamond tips used for microscratch testing. As a result, for many material combinations the exact determination of the critical load was difficult or impossible, especially in cases of thin or multi-layered coatings.

OBJECTS OF THE INVENTION

The object of the present invention is to provide a scratch test indenter, suitable for microanalysis of coatings and thin films, which allows for simultaneous precision acoustic, electrical and mechanical measurements of the indenter-coating interactions, and thus for precision determination of the critical load of, or time till, coating failure, with improved measurement data correlation, which does not produce stresses deep in the substrate under the coating, which does not need preparation of special test samples, and is not very sensitive to the deviations in its position with respect to the tested surface. Another object is to provide a microscratch test method, which is simple, reliable, applicable for thin films and coatings due to a smaller effect of substrate properties on the test data, and which produces accurate and repeatable test results, even for multi-layered materials, by monitoring simultaneously friction, acoustic and electrical characteristics of the moving indenter-coating contact and correlating all the measured data.

SUMMARY OF THE INVENTION

An indenter and method for a microscratch test of durability of materials, including resistance of coating films to delamination. The indenter has a prism-like micro-blade shape and is defined by a front side, a rear side, a first lateral side, and a second lateral side. The first lateral side and the second lateral side converge and form at their intersection an edge that extends from the front side to the rear side. An angle between the edge and the front side is sharp, while an angle between the first lateral side and the second lateral side is rounded with a radius. For a microscratch test, the blade-like indenter is installed with a selected angle of attack between the front side and the test surface, a relative movement is created between the indenter and the test sample, with simultaneous mechanical, acoustical, and electrical measurements of the indenter-surface interactions. The results of these independent measurements are compared and analyzed for precision determination of the critical test parameters corresponding to surface (coating) failures and thus characterize the durability of the test sample by both or either the scratch resistance of its surface and the delamination resistance of its layers.

DETAILED DESCRIPTION OF THE INVENTION

Figure 1:
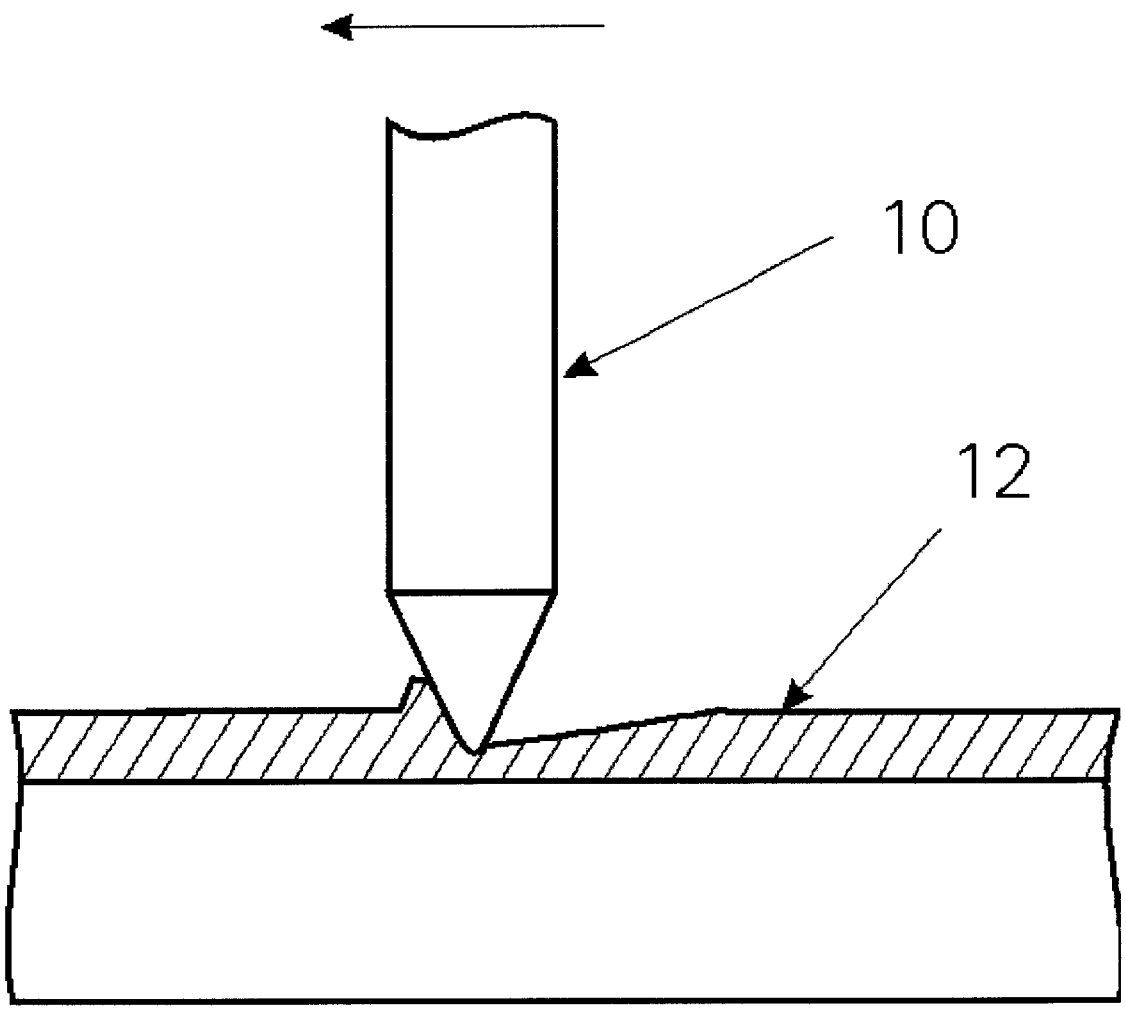
FIG. 1 is a side sectional view of a known sharp point indenter, or tip, used for microscratch test.
Figure 2:
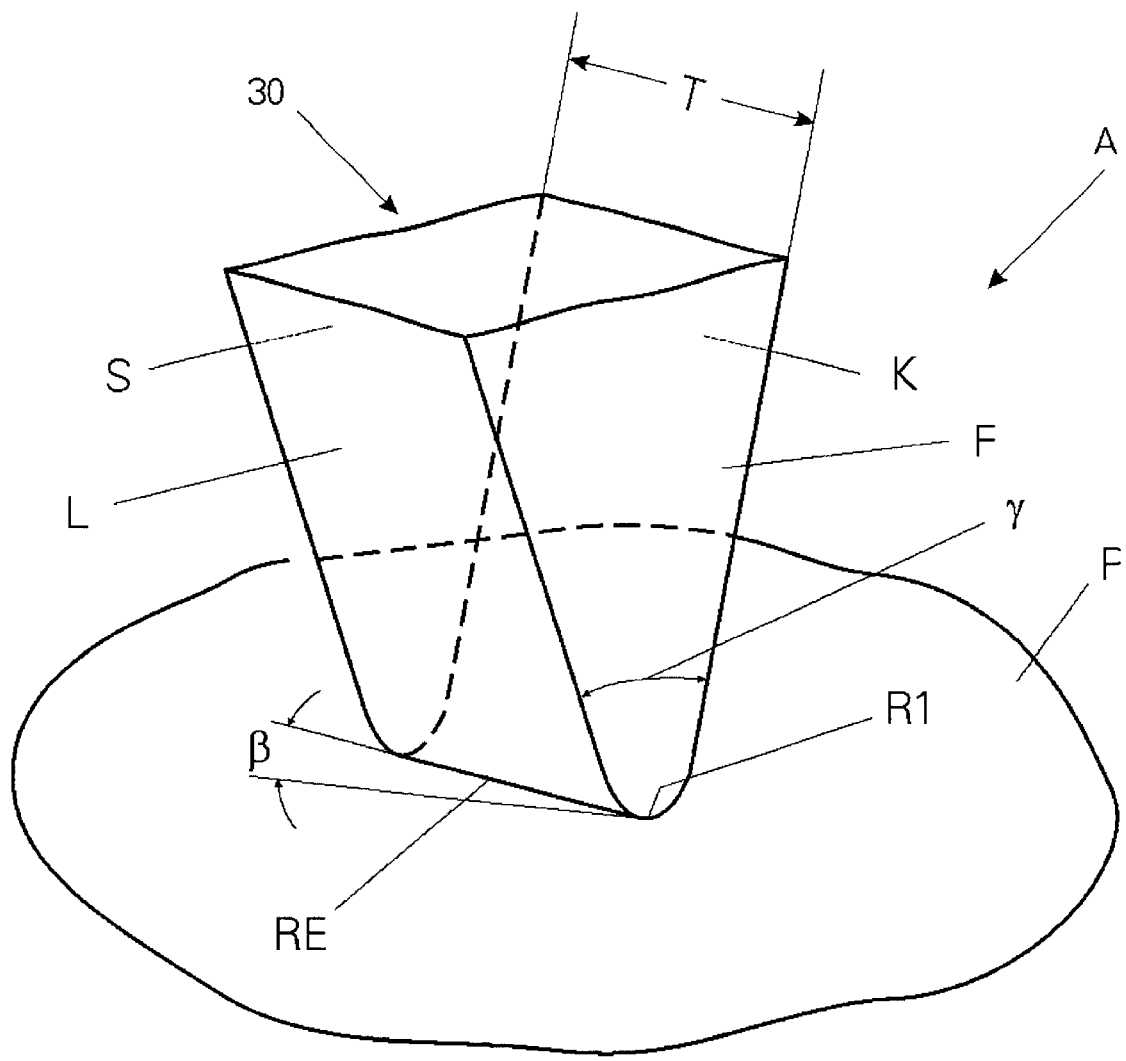
FIG. 2 is a three-dimensional view of a microscratch test micro-blade indenter of the present invention.
Figure 3:
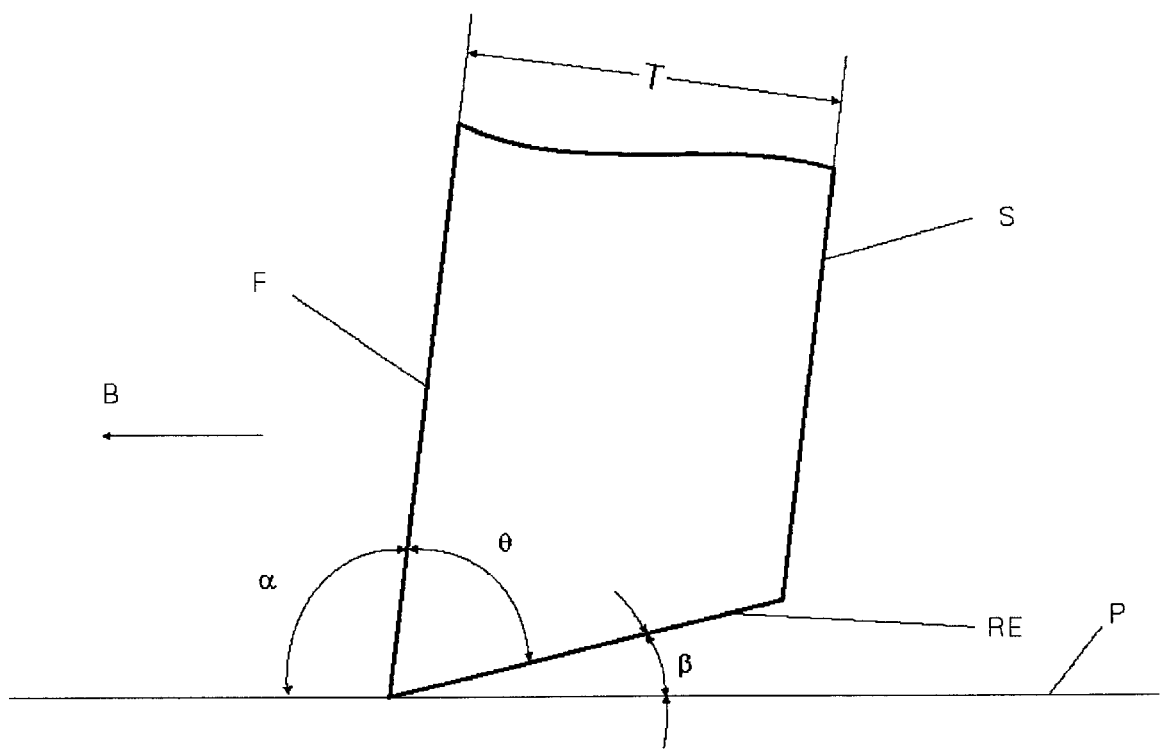
FIG. 3 is a view of the microscratch test micro-blade indenter of the present invention in the direction of arrow A in FIG. 2.

A three-dimensional view of the microscratch indenter of the present invention is shown in FIG. 2. The contact geometry of the blade-like indenter has been selected based on contact stress analysis and large amount of experiments. One of the chosen materials for the indenter is tungsten-carbide, since it is not only hard, but also conductive, which is critical for measuring the electric contact resistance across the interface between the indenter and the tested surface. As can be seen from FIG. 2, the microscratch indenter 30 comprises a prism-like body defined by a front side F, a rear side S, a first lateral side L and a second lateral side K. The first lateral side L and the second lateral side K converge and form at their intersection an edge RE that extends from the front side F to the rear side S. As shown in FIG. 3, which is a side view of the indenter 30 in the direction of arrow A in FIG. 2, an angle $\theta$ between the edge RE and the front side F is sharp, while an angle $\gamma$ between the first and second lateral sides (FIG. 2) is rounded with a radius R1.

The angle $\theta$ can be selected within the range of 10° to 160°. The angle $\gamma$ can be selected within the range of 15° to 170°. Radius R1 can be within the range of 0.1 mm to 3 mm.

Although the indenter 30 is shown as a body having a uniform thickness T, this dimension is not critical, and on its side (not shown) opposite to the edge RE it may have configuration convenient for attachment to a tester.

Test geometry should be considered in combination with the angles formed between the facets or sides and the edge of the micro-blade and the surface of an object being tested. In this respect one can refer to FIG. 3, where $\alpha$ designates a front attack angle, which is formed between the front side F of the indenter 30, that faces the direction of movement during the test, and the surface P of the material being tested. The indenter 30 also forms a back attack angle $\beta$ between its relief edge RE and the surface P. Arrow B shows a direction of movement during scratching.

The aforementioned two attack angles are crucial for successful evaluation of scratch resistance and adhesion of thin film coatings. The choice of both attack angles depends on the thickness and hardness of the coating films. The back angle $\beta$ is found to be in the range of 5° to 85°, preferably from 10° to 30° for most materials. The front angle $\alpha$ should be in the range of 10° to 170°, preferably in the range of 60° to 120°. Both front and back angles affect the contact stress distribution and test results.

Microscratch tests were conducted for determining the durability of multi-micron-thick elastomer coatings on metal surfaces of ink-jet cartridges for printers, as well as of few-nanometer-thick carbon coatings on magnetic disks for hard disk drives. We used both the conventional sharp diamond tip of 10 micron radius and the micro-blade indenters of the present invention made of tungsten carbide and a polycrystalline diamond and having the following geometry: $\gamma=60°$, R1=0.4 mm, $\beta=10°$, $\alpha=90°$.

The indenters were installed into a special holder of a micro-tribometer mod. UMT, developed and manufactured by Center for Tribology, Inc., Campbell, Calif., USA. The tester has a frame that supports a moveable carriage with guideways, having a loading unit for application of a normal load. The tester is equipped with a moving stage that supports a test material, as well as with a measuring system for simultaneous real-time monitoring and comparative analysis of a friction force $F_x$, normal load $F_z$, coefficient of friction COF as their ratio, electric contact resistance ECR and acoustic emission AE. In each test, the indenter was slowly moved against a coated test surface, while normal load was continuously gradually increased.

Figure 4:
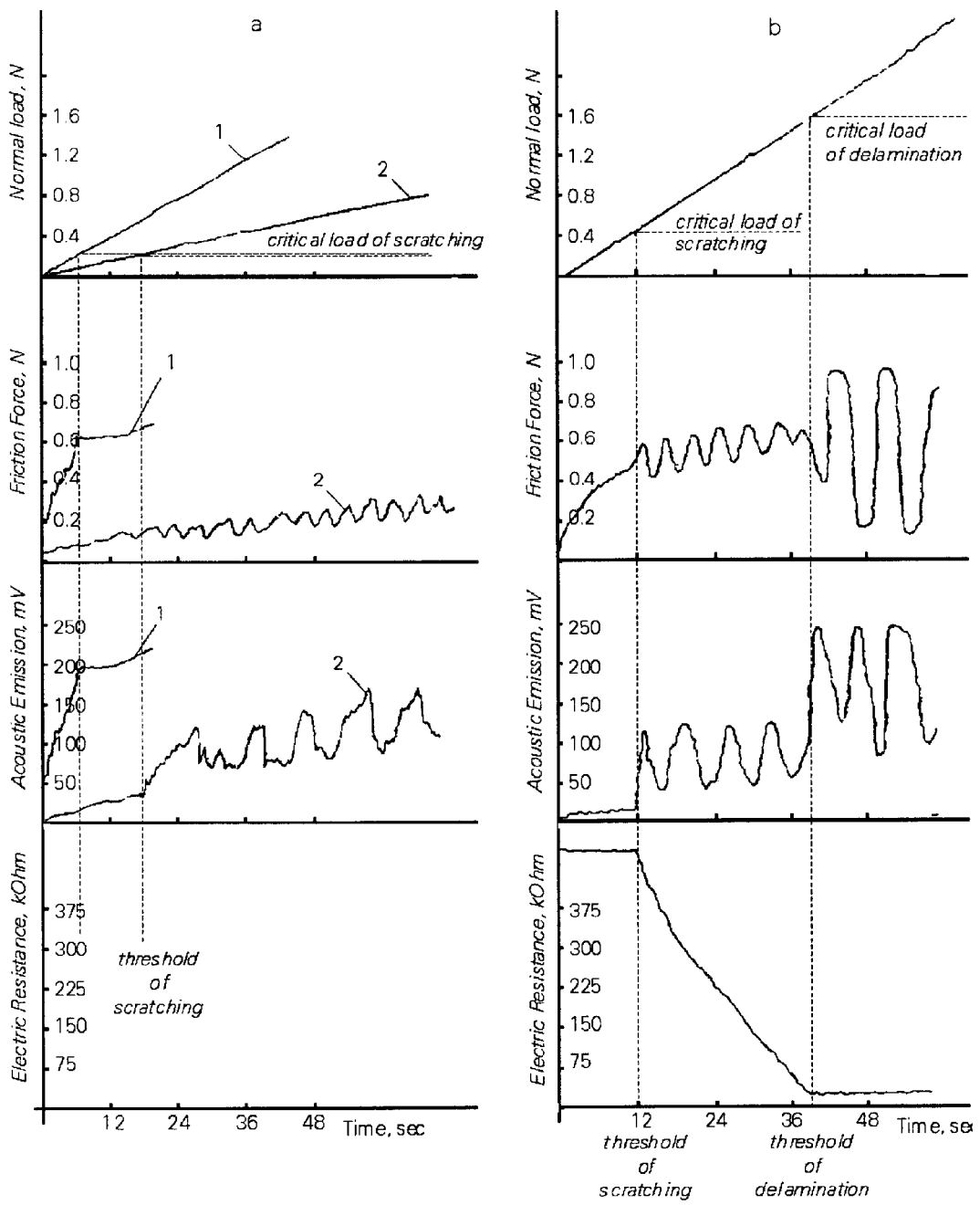
FIG. 4 shows microscratch test data on elastomer-coated metal surfaces with a known point indenter (a) and the micro-blade indenter of present invention (b).

FIG. 4 presents typical results for the elastomer coatings, with the known point indenter (FIG. 4a) and the micro-blade-like indenter per present invention (FIG. 4b). The abscissa axes show time in seconds, the ordinate axes show a linearly increasing normal load, as well as three response signals of friction force, acoustic emission and electrical contact resistance.

Under the same applied loads (FIG. 4a—curves 1), the point indenter develops higher contact pressures and breaks the coating right away, so the loads on the point indenter had to be reduced; however, the small reduced loads (FIG. 4a—curves 2) have led to the reduced both precision and repeatability of the measurements. Also, the absence of electrical resistance measurements did not allow for improved accuracy of determination of the critical load. Although with less accuracy, it was still possible to measure scratch resistance with the point indenter. However, it was impossible to observe coating delamination and measure coating adhesion to the substrate, as the indenter was too sharp and small to delaminate significant areas of the coating.

The microscratch test per the present invention (FIG. 4b) allowed to clearly observe three different modes of test surface interactions with the micro-blade-like indenter. At small normal loads, the coating was deformed with no wear particles produced. Then at the critical load of scratching there was a well-defined transition from deformation to microscratching, after which sub-micron wear debris were produced. Then at the critical load of delamination there was another threshold, defining transition to delamination with substantial multi-micron particles being produced and chunks, or areas, of the coating coming off the substrate. All the monitored signals, namely, friction force, acoustic emission and electrical contact resistance, have fully correlated between them in both defining the moments of the thresholds and the coating modes of failure. As shown in the drawings, the interaction of the indenter with the surface of the test material was monitored as a function of time or force. Furthermore, durability and adhesive properties of the test material were evaluated by analyzing the monitored interactions.

Figure 5:
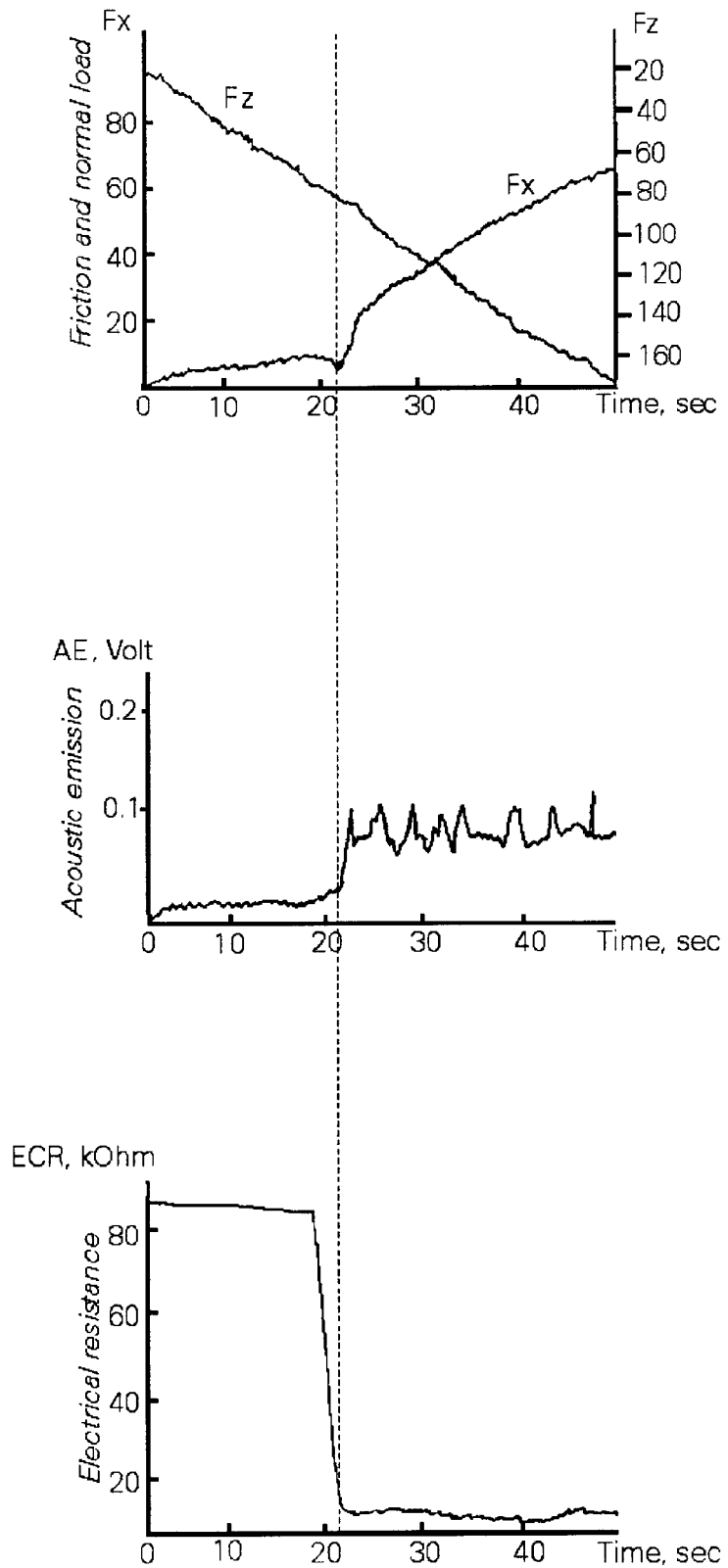
FIG. 5 show microscratch test data measured on carbon-overcoated magnetic disks, with simultaneous use of mechanical, acoustical, and electrical signals.

FIG. 5 shows an example of microscratch test data on a magnetic disk with a 5-nm overcoat of a diamond-like carbon. Like in FIG. 4, the abcissa axes show time in seconds, the ordinate axes show normal load, friction force, acoustic signal and electrical contact resistance.

While the normal load was increased, the coating film was broken and cut through by the indenter at the moment of 22 seconds after beginning of the test, corresponding to a critical load of 80 grams. At this critical load, friction force shifted to higher values with a different, steeper slope. At exactly the same time, electrical contact resistance dropped to practically zero, because the indenter made contact with the conductive metal under-layer.

Meanwhile, acoustic emission increased and fluctuated more after the load exceeded the critical value, though its increase was not always as sharp as that of both friction and electrical signals. It looks like for the ultra-thin carbon films, the acoustic signal may still be a characteristic of their failure mode, but the friction and electric signals may be more informative for determination of the exact moment of threshold.

For comparison, similar tests were conducted with the use of a known conventional diamond tip, without electrical signal monitoring. As can be seen from FIG. 4(a), in the case of a conventional diamond tip, the high contact pressures from the point indenter produced immediate failure of the thin coating film. Therefore much smaller loads were required. At the very low load levels, however, the test data was neither informative nor repeatable.

Analysis of the test results has confirmed that the micro-blade of the invention with two variable attack angles is the most effective indenter for scratch resistance and adhesion evaluations, as compared to conventional indenters, such as sharp conical tips. The fact that the contact stress distribution produced by the micro-blade is concentrated mostly within the thin coating film, without penetrating deep into the substrate, allows to compare the scratch and delamination resistance of thin films themselves, with the minimum effect of the underlying layers or substrate. Contact stress analysis showed that with the conical point indenter, or tip, the contact stress is distributed well beyond sub-micrometer level from the surface, which is not suitable for studying processes that occur in thin films.

It should be noted that in some tests, some of the coatings did not produce good correlation in threshold determination between all the monitored signals. Due to either structure of test materials or specific surface treatments, for some of them acoustic signal was not informative, for the others the electrical signal was not reflective of the surface interactions and failures. We then used a rule that the threshold is defined when at least two out of the three signals show the transition and are in agreement. This is why measuring all the mechanical, acoustical and electrical signals allow for the most comprehensive test method to evaluate the durability of different materials and surface treatments.

Thus it has been shown that the method of microscratch test of the invention comprises providing a microscratch blade-like indenter of the type described above, bringing the indenter in contact with the surface of the test material, positioning the indenter with respect to test material surface to form specified attack angles between the sides of the indenter and the test material surface, applying a force to the indenter for indenting it into the surface, causing a relative movement between the indenter and the test material, monitoring the interaction of the indenter with the test material surface as a function of time or force, and evaluating durability and adhesive properties of the test material by analyzing the monitored interactions. The step monitoring comprises simultaneous measurements of several characteristics and parameters in various combinations, e.g., both normal load and the friction response force resisting said relative movement, thus measuring a coefficient of friction during testing, or acoustic emission from a contact between the indenter and the test material surfaces and the electrical characteristics, etc.

It has been also shown that the invention provides a microscratch test indenter which is suitable for microanalysis, allows for simultaneous accurate acoustic, electrical and mechanical measurements of both normal loads and friction forces with improved measurement data correlation, does not produces stresses penetrating through the coating into the substrate, does not need preparation of special test samples, and is not very sensitive to the deviations in the position of the test blade with respect to the surface of the test material. The invention also provides a microscratch test method, which is simple, reliable, produces accurate and repeatable test results, and improves the accuracy of durability evaluation by providing a high degree of correlation of the simultaneously monitored mechanical, electrical and acoustical signals.

Although the invention has been described with reference to specific embodiment, it is understood that this embodiment should not be construed as limiting the application of the invention, and various changes and modifications are possible, provided they do not depart from the scope of the patent claims. For example, the micro-blade indenter can be made of materials other than those indicated in the specification; these materials can be conductive or non-conductive, such as crystalline materials, e.g., hafnium or zirconium oxides with crystal facets sharpened at the angles corresponding to the front and back attack angles specified by the present invention. In the electrical measurements, electrical impedance or capacitance can be measured instead of resistance. In the data analysis, durability evaluation can be performed, using either critical time to failure or critical load or critical number of cycles.

What is claimed is:

1. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and a said surface, and a back attack angle between said edge and said surface;

applying a force to said blade-like indenter for indenting it into said surface, and a relative movement between said blade-like indenter and said test material;

monitoring the interaction of said blade-like indenter and said surface as a function selected from a function of time and function of force;

evaluating said durability and adhesive properties of said test material by analyzing said monitored interactions, wherein said back attack angle is in the range of 5° to 85°.

2. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said steps of monitoring comprises simultaneous measurements of both normal load perpendicular to said surface, and the friction response force resisting said relative movement, thus measuring a coefficient of friction during testing, and said step of evaluating includes an analysis of said coefficient of friction.

3. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said step of monitoring comprises simultaneous measurements of a normal load perpendicular to said surface, a friction response force resisting said relative movement, and acoustic emission from a contact between said blade-like indenter and said surface, and said steps of evaluating includes a comparitive analysis of both said coefficient of frictions and said acoustic emission.

4. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said step of monitoring comprises measurements of acoustic emission from a contact between said blade-like indenture and said surface, and said step of evaluating includes an analysis of said acoustic omission, and wherein said acoustic emission is characterized by an acoustic frequency spectrum which has a lower part corresponding to mechanical noises and a higher part corresponding to said interaction, said measurements comprising filtering said lower part out from said higher part.

5. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said step of monitoring comprises measurements of acoustic emission from a contact between said blade-like indenture and said surface, and said step of evaluating includes an analysis of said acoustic omission, and wherein said acoustic emission is characterized by an acoustic frequency spectrum, which has a lower part corresponding to mechanical noises and a higher part corresponding to said interaction, said step of evaluating comprising analyzing said interaction by filtering said lower part from said higher part and using only said upper part for analysis.

6. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said step of monitoring comprises measurements of acoustic emission from a contact between said blade-like indenture and said surface, and said step of evaluating includes an analysis of said acoustic omission, and wherein said acoustic emission is characterized by an acoustic frequency spectrum, which has a lower part corresponding to mechanical noises and a higher part corresponding to said interaction, said step of monitoring comprising filtering said lower part out from said higher part and using only said upper part for analysis.

7. A method of microscratch test for testing durability and adhesive properties of a test material, comprising the steps of:

providing a microscratch blade-like indenter having a body defined by a front side, a rear side, a first lateral side and a second lateral side, said first lateral side and said second lateral side converging and forming at their intersection an edge that extends from said front side to said rear side, an angle between said edge and said front side being sharp, and an angle between said first lateral side and said second lateral side being rounded;

bringing said blade-like indenter in contact with a surface of said test material;

positioning said blade-like indenter with respect to said surface of said test material to form a front attack angle between said front side and said surface, and a back attack angle between said edge and said surface;

applying a force to said blade-like indenter for indenting it into said surface;

applying a relative movement between said blade-like indenter and said test material;

monitoring the interaction of said indenter and said surface as a function selected from a function of time and a function of force;

evaluating said durability and adhesive properties of said test material by analyzing said monitored interactions, wherein said step of monitoring comprises measurements of acoustic emission from a contact between said blade-like indenture and said surface, and said step of evaluating includes an analysis of said acoustic omission, and wherein said acoustic emission is characterized by an acoustic frequency spectrum, which has a lower part correspondingly to mechanical noises and a higher part corresponding to said interaction, said step of monitoring comprising filtering said lower part out from said higher part and using only said upper part for monitoring.

8. The method of claim 2, wherein said test material has a substrate and a coating layer, said coating layer having electric properties different from those of said substrate, said step of monitoring comprises measuring a contact electric resistance in an circuit passage through said blade-like indenter and said test material surface via said coating layer, generating an electric signal in response to said measuring, and analyzing said electric signal in said step of evaluating.

9. The method of claim 7, wherein said step of monitoring comprises simultaneous measurements of said normal load, said friction response force, and said electrical resistance, and said step of evaluating comprises a comparative analysis of both said coefficient of friction and said electrical signal.

10. The method of claim 7, wherein said microscratch test blade-like indenter is made of an electrically conductive material.

11. The method of claim 7, wherein said angle between said edge and said front side is within the range of 10° to 160°.

12. The method of claim 7, wherein said angle between said first lateral side and said second lateral side is within the range of 15° to 170°.

13. The method of claim 8, wherein said radius is within the range of 0.1 mm to 3 mm.

* * * * *